(12) United States Patent
Guo et al.

(10) Patent No.: US 11,009,443 B2
(45) Date of Patent: May 18, 2021

(54) METHOD FOR DYNAMIC IMBIBITION CAPACITY OF SHALE

(71) Applicant: SOUTHWEST PETROLEUM UNIVERSITY, Chengdu (CN)

(72) Inventors: Jianchun Guo, Chengdu (CN); Liang Tao, Chengdu (CN); Chi Chen, Chengdu (CN); Zhihong Zhao, Chengdu (CN); Ming Li, Chengdu (CN); Pengcheng Tang, Chengdu (CN)

(73) Assignee: SOUTHWEST PETROLEUM UNIVERSITY, Chengdu (CN)

( * ) Notice: Subject to any disclaimer, the term of this patent is extended or adjusted under 35 U.S.C. 154(b) by 0 days.

(21) Appl. No.: 16/937,608

(22) Filed: Jul. 24, 2020

(65) Prior Publication Data

US 2020/0355598 A1    Nov. 12, 2020

(30) Foreign Application Priority Data

Sep. 4, 2019  (CN) .......................... 201910833172.X

(51) Int. Cl.
| | | |
|---|---|---|
| *G01N 15/08* | (2006.01) | |
| *E21B 49/02* | (2006.01) | |
| *G01N 33/24* | (2006.01) | |
| *E21B 43/26* | (2006.01) | |

(52) U.S. Cl.
CPC ......... *G01N 15/0826* (2013.01); *E21B 49/02* (2013.01); *G01N 33/24* (2013.01); *E21B 43/2607* (2020.05)

(58) Field of Classification Search
CPC ..... E21B 43/2607; E21B 49/02; G91N 15/08; G91N 15/0826; G91N 15/0873; G91N 33/24
See application file for complete search history.

(56) References Cited

U.S. PATENT DOCUMENTS

| | | | | |
|---|---|---|---|---|
| 6,247,358 | B1 * | 6/2001 | dos Santos | ............. E21B 25/08 |
| | | | | 166/282 |
| 10,365,200 | B2 * | 7/2019 | Liu | ........................ G01N 33/24 |
| 10,837,278 | B2 * | 11/2020 | Zhu | ........................ G01N 33/24 |
| 2015/0059447 | A1 * | 3/2015 | Rickards | ................ G01N 19/00 |
| | | | | 73/61.41 |
| 2016/0341652 | A1 * | 11/2016 | Liu | ........................ G01N 15/08 |
| 2019/0226970 | A1 * | 7/2019 | Dusterhoft | .............. E21B 49/00 |
| 2019/0293542 | A1 * | 9/2019 | Liu | ........................ G01N 15/08 |
| 2021/0079789 | A1 * | 3/2021 | Zhi | ........................ G01V 3/14 |

FOREIGN PATENT DOCUMENTS

| | | | | |
|---|---|---|---|---|
| CN | 205038132 U | | 2/2016 | |
| CN | 106644871 A | * | 5/2017 | ......... G01N 15/0826 |
| CN | 109374495 A | | 2/2019 | |

* cited by examiner

*Primary Examiner* — John Fitzgerald

(57) ABSTRACT

An experimental test method for dynamic imbibition capacity of shale is provided. The method includes the following steps: core preparation; physical parameter test of shale; experimental loading conditions are determined according to formation stress, formation temperature and hydraulic fracturing parameters; and a dynamic imbibition saturation is defined to characterize a dynamic imbibition amount. Various factors, such as fracturing fluid flow, formation confining pressure, formation temperature and fluid pressure, are used to obtain change rules of dynamic imbibition with time under different construction parameters in shale fracturing process.

1 Claim, 2 Drawing Sheets

METHOD FOR DYNAMIC IMBIBITION CAPACITY OF SHALE

TECHNICAL FIELD

The present invention relates to the field of petroleum and natural gas engineering, in particular to an experimental testing device and method for the dynamic imbibition capacity of the shale in the process of the shale hydraulic fracturing.

DESCRIPTION OF PRIOR ART

The shale gas is commercially exploited in North America as an unconventional oil and gas resource. The multi-stage fracturing technology for the horizontal well is the key technology to realize the shale gas revolution. In recent years, the exploration and field test has been conducted in major domestic oil and gas fields based on the successful experience in multi-stage fracturing transformation of the horizontal well abroad, which has achieved favorable stimulation effects.

The fracturing & stimulation of the shale gas reservoirs at home and abroad shows that the flowback rate of the fracturing fluid is very low, generally lower than 50%, lower than 20% in Eagle Ford basin in the United States, lower than 50% in Barnett basin, and even lower than 3% in Fuling shale gas reservoir in China (Zhang Tao, Li Xiangfang, Yang Lifeng. Effect of shut-in timing on flowback rate and productivity of shale gas wells [J]. Natural Gas Industry, 2017, 37 (8): 48-58). A large amount of fracturing fluid is left in the reservoir, but the productivity increases after a period of well shut-in, resulting in "low flowback rate and high productivity", which has attracted a wide attention of the industry.

The shale is characterized by complex components and special microstructures, especially high clay content, high salinity and ultra-low water saturation. The water imbibition will have a special effect on the microstructure, thus affecting the productivity of shale gas wells. In order to explain the special flowback in shale gas wells, it is first necessary to study the imbibition mechanism of the shale. The dynamic imbibition during shale fracturing is the imbibition of the fluid in shale matrix when it flows in hydraulic fractures. Learned from a great deal of statistics data on oil fields, shale gas wells are developed by large-scale SRV fracturing technology. Tens of thousands of cubic meters of water-based fracturing fluid are injected into the formation. During the whole fracturing process, the fracturing fluid is imbibited into the shale reservoir when it flows in the formation for a long time, which has an important impact on the total imbibition amount of the shale, and furthermore affects the flowback rate of the fracturing fluid. Therefore, it is of great significance to accurately measure and quantify the imbibition capacity of the fluid when it flows in the formation by using the laboratory experiment method for understanding the flow mechanism of the fracturing fluid in shale reservoirs, identifying the main contribution stage of the shale imbibition, and optimizing the flowback system. In the process of the shale fracturing, fluid injection and displacement, formation confining pressure, formation temperature and fluid injection pressure all have an impact on the imbibition amount, but these factors have not been taken into account in the current experimental studies. At present, most studies focus on the shale spontaneous imbibition. The shale imbibition capacity (Yang L, Ge H, Shi X, et al. Experimental and numerical study on the relationship between water imbibition and salt ion diffusion in fractured shale reservoirs [J]. Journal of Natural Gas Science and Engineering, 2017, 38: 283-297) is tested by using the scale to measure the changes in the mass of the shale with time after the spontaneous imbibition, and the spontaneous imbibition amount (Li X, Teklu T, Abass H, et al The Impact of Water Salinity/Surfactant on Spontaneous Imbibition through Capillarity and Osmosis for Unconventional IOR [C]. SPE Unconventional Resources Technology Conference, 1-3 August, San Antonio, Tex., USA, 2016. URTEC-2461736-MS.) at different time is calculated by the numerical simulation method and the shale matrix spontaneous imbibition which is established with consideration of the fluid pressure, the seepage pressure and the capillary pressure.

However, these methods do not consider the impact of the fluid flow in hydraulic fractures, formation confining pressure, formation temperature, fluid injection pressure and other factors on shale imbibition capacity in the process of the shale fracturing under the actual formation conditions, so there is a lack of quantitative characterization of the dynamic imbibition capacity. Therefore, it is necessary to study the test method of the shale dynamic imbibition capacity under the condition of the fluid flow, and to improve the important support for understanding the flow rules of the fracturing fluid in shale reservoirs and optimizing the shut-in time.

SUMMARY OF THE INVENTION

The purpose of the present invention is to provide an experimental testing device for the dynamic imbibition capacity of the shale and a method for testing and analyzing the shale dynamic imbibition capacity with the device.

An experimental testing device for the dynamic imbibition capacity of the shale, comprising a formation temperature simulation system, a formation confining pressure simulation system, an injection pressure simulation system, and a fluid flow simulation system.

The formation temperature simulation system is a heater, which is used to adjust the temperature of the reaction kettle.

The formation confining pressure simulation system is a confining pressure pump, which is used to simulate the formation confining pressure.

The injection pressure simulation system comprise a constant-speed and constant-pressure pump, an outlet valve of constant-speed and constant-pressure pump, an intermediate container, and an outlet valve of intermediate container, all of which are connected to the reaction kettle in order. The constant-speed and constant-pressure pump injects fluid under pressure into the reaction kettle.

The fluid flow simulation system comprises a motor, a rotor and rotor blades. The height of the rotor blade is aligned with the core axis. The motor drives the rotor blade to rotate to drive the fluid under pressure in the reaction kettle to flow.

Further, the experimental testing device also comprises a vacuum pump and an inlet valve of the vacuum pump, which are connected to the reaction kettle in order.

Further, the experimental testing device further comprises a cylindrical spacer where a hole is arranged at the center for fluid flowing and the core is in contact with the fluid at one end and in contact with the cylindrical spacer at the other end.

Further, a guide groove is arranged at the contact surface between the cylindrical spacer and the core.

Further, the inner cavity of the reaction kettle is cylindrical, with a diameter of 7.6 cm.

Further, the rotor blade has a half-length of 3.6 cm, a thickness of 0.2 cm, and a width of 3 cm.

Further, the measurement accuracy of the constant-speed and constant-pressure pump is not less than 0.001 mL/min, and the continuous measurement period is not less than 24 h.

An experimental test method for the dynamic imbibition capacity of the shale, comprising the following steps in order:

(1) Core preparation: The core is made of the downhole rock column in the shale reservoir section or outcrop in the same formation; the imbibition area A of the core is calculated according to the end size of the core, the core length is the experimental measurement length L, and the standard core is dried in the dryer to a constant weight;

(2) Physical parameter test of the shale: The porosity φ of the dried core mentioned in Step (1) is tested by a porosity tester with helium as the working medium.

(3) The experimental loading conditions are determined according to the formation stress, the formation temperature and hydraulic fracturing parameters. The specific method is to determine the confining pressure loaded in the experiment with the formulas (1) to (4). The reservoir temperature is the experimental temperature, and the fluid injection pressure is determined by the formula (5).

$$\sigma'_z = \sigma_z - \alpha P_p \quad (1)$$

$$\sigma'_H = \sigma_H - \alpha P_p \quad (2)$$

$$\sigma'_h = \sigma_h - \alpha P_p \quad (3)$$

$$\sigma_C = (\sigma'_z + \sigma'_H + \sigma'_h)/3 \quad (4)$$

$$P_{inj} = P_{ISI} - P_p \quad (5)$$

In the formulas, $\sigma'_z$ is the vertical effective stress, in MPa; $\sigma'_H$ is the maximum horizontal effective principal stress, in MPa; $\sigma'_h$ the minimum horizontal effective principal stress, in MPa; $\sigma_z$ is the vertical stress, in MPa; $\sigma_H$ is the maximum horizontal principal stress, in MPa; $\sigma_h$ the minimum horizontal principal stress, in MPa; $\alpha$ is the effective stress coefficient, in decimal; $\sigma_c$ is the experimental confining pressure, in MPa; $P_{inj}$ is the fluid injection pressure, in MPa; $P_{ISI}$ is the bottom-hole instantaneous shut-in pressure for the hydraulic fracturing, in MPa; $P_P$ is the formation pore pressure, in MPa.

(4) The fracturing fluid is prepared according to the fracturing fluid formula on the construction site, and poured into the intermediate container of the constant-speed and constant-pressure pump.

(5) The core after the porosity test in Step (2) is put into the core holder, and loaded with an initial confining pressure by the confining pressure pump.

(6) The reaction kettle, the core and the core holder are heated by the heater to the experimental temperature determined in Step (3).

(7) The air in the pipe and the reaction kettle is completely pumped out by the vacuum pump, then the inlet valve of the vacuum pump is closed, and the fracturing fluid in the intermediate container in Step (4) is pumped by the constant-speed and constant-pressure pump into the reaction kettle.

(8) The linear velocity of the fracturing fluid on the fracture surface is calculated with the formula (6) according to the fracturing displacement of the shale gas well, the shale reservoir thickness, and the hydraulic fracture width. The loading velocity is calculated with the formula (7) according to the relationship between the linear velocity and the rotation speed. The motor is switched on to load the rotor to the calculated rotation speed.

$$v = \frac{Q}{hw} \quad (6)$$

$$n = \frac{v}{2\pi r} \quad (7)$$

In the formulas, v is the linear velocity of fluid, in m/s, Q is the fracturing displacement of the shale gas well, in m³/min, h is the thickness of the reservoir where the shale gas well is located, in m, W is the hydraulic fracture width, in m, n is the loading speed, in rad/min, and r is the rotor radius, in m.

(9) The injection pressure of the constant-speed and constant-pressure pump is set according to the loading pressure of the confining pressure pump that is determined in Step (3) and the determined injection pressure. At the same time, the control computer of the constant-speed and constant-pressure pump records the injected fluid volume once every three minutes. The cumulative volume of each time node is the dynamic imbibition amount of the shale at that time. The test time is the average single-stage fracturing time of the shale gas well.

(10) According to the dynamic imbibition amount measured in Step (9), the dynamic imbibition saturation I is defined to characterize the dynamic imbibition amount, that is, the percentage I of the dynamic imbibition amount to the core pore volume, expressed as follows:

$$I = \frac{V}{\varphi A L} \times 100\% \quad (8)$$

In the formula: I is the dynamic imbibition saturation, in %, V is the dynamic imbibition amount, in cm³, A is the imbibition area, in cm², L is the core length, in cm, and φ is the porosity, in %.

Compared with the prior art, the present invention has the following beneficial effects:

(1) The present invention designs an innovative experimental device and a test method for the shale dynamic imbibition capacity considering various factors such as the fracturing fluid flow, the formation confining pressure, the formation temperature and the fluid pressure.

(2) The present invention can truly reflect and quantitatively test the change rule of the dynamic imbibition with time under different construction parameters in the shale fracturing process under different formation conditions, and define the dynamic imbibition saturation to quantitatively characterize the shale dynamic imbibition capacity, which has an important guiding role in understanding the imbibition rule of the fracturing fluid in shale reservoirs under the actual formation conditions.

DETAILED DESCRIPTION OF THE PREFERRED EMBODIMENTS

Figure 1:
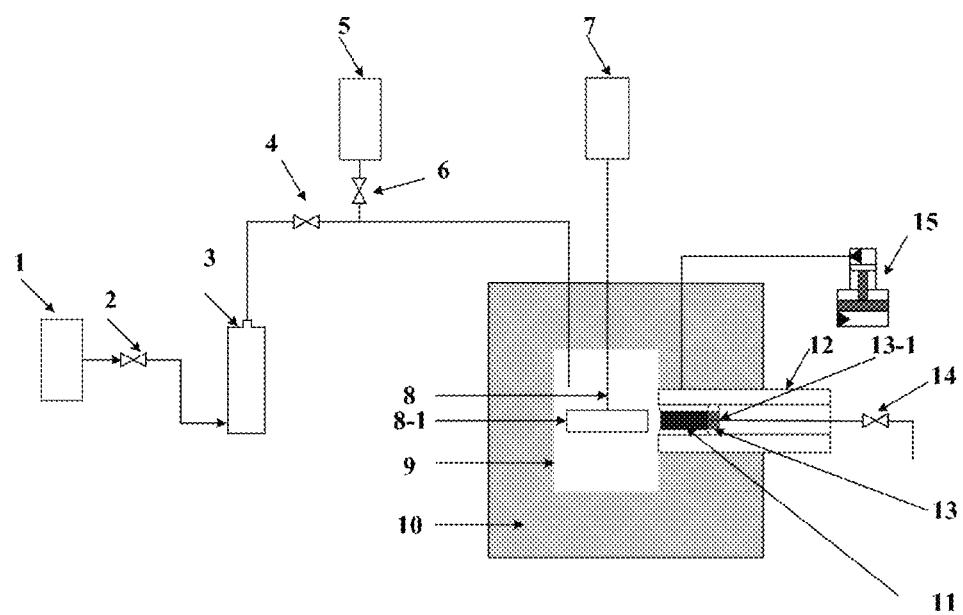
FIG. 1 is a schematic diagram of the experimental testing device for the dynamic imbibition capacity of the present invention.

The description that follows, with reference to the appended figures and the detailed description of the preferred embodiments of the present invention, will allow the present invention to be understood more clearly. However, the specific embodiments of the present invention described herein are only for the purpose of explaining the present invention, and should not be construed as limiting the present invention in any way. Under the guidance of the present invention, those skilled in the art can conceive of any possible variations based on the present invention, which should be considered as falling within the scope of the present invention.

The experimental testing device for the dynamic imbibition capacity of the shale consists of the constant-speed and constant-pressure pump (1), the outlet valve (2) of the constant-speed and constant-pressure pump, intermediate container (3), the outlet valve (4) of the intermediate container, the vacuum pump (5), the inlet valve (6) of the vacuum pump, rotor (8), the rotor blade (8-1), the reaction kettle (9), the heater (10), the core (11), the core holder (12), the cylindrical spacer (13), the outlet valve (14) of the core holder, and the confining pressure pump (15).

The heater (10) constitutes the formation temperature simulation system of the experimental testing device. The confining pressure pump (15) constitutes the formation pressure simulation system of the experimental testing device. The injection pressure simulation system of the experimental testing device comprises the constant-speed and constant-pressure pump (1), the outlet valve (2) of the constant-speed and constant-pressure pump, the intermediate container (3), and the outlet valve (4) of the intermediate container. The fluid flow simulation system of the experimental testing device consists of the motor (7), the rotor (8), and the rotor blade (8-1).

In the experiment, the core (11) is placed in the core holder (12), with one end in contact with the fluid and the other end in contact with the cylindrical spacer (13). The confining pressure is applied to the core (11) by the confining pressure pump (15) during the experiment.

A guide groove is arranged at the contact surface between the cylindrical spacer (13) and the core. A hole (13-1) is arranged at the center of the cylindrical spacer (13) for fluid flowing, and the fluid can flow to the outlet valve (14) of the core holder through the hole.

A volume of 1,000 mL is preferred for the reaction kettle (9). The inner cavity of the reaction kettle is cylindrical, with a diameter of 7.6 cm.

The rotor blade (8-1) has a half-length of 3.6 cm, a thickness of 0.2 cm, and a width of 3 cm. The height direction of the rotor blade (8-1) shall be aligned with the axis of the core (11). The rotor blade can rotate to drive the fluid to simulate the effect of underground fluid flow on the dynamic imbibition of the shale.

The test of the dynamic imbibition capacity of the shale by using experimental testing device disclosed in the present invention comprises the following steps in order:

(1) Core preparation: Downhole cores in the shale reservoir section or outcrops of the same stratum are made into standard cores with a diameter of 2.5 cm and a length of 5 cm; the imbibition area A of the core is calculated according to the end size of the core, the core length is the experimental measurement length L, and the standard core is dried in the 100° C. dryer to a constant weight;

(2) Physical parameter test of the shale: The porosity φ of the dried core mentioned in Step (1) is tested by a porosity tester with helium as the working medium.

(3) The experimental loading conditions are determined according to the formation stress, the formation temperature and hydraulic fracturing parameters. The specific method is to determine the confining pressure loaded in the experiment with the formulas (1) to (4). The reservoir temperature is the experimental temperature, and the fluid injection pressure is determined by the formula (5).

$$\sigma'_z = \sigma_z - \alpha P_p \tag{1}$$

$$\sigma'_H = \sigma_H - \alpha P_p \tag{2}$$

$$\sigma'_h = \sigma_h - \alpha P_p \tag{3}$$

$$\sigma_c = (\sigma'_z + \sigma'_H + \sigma'_h)/3 \tag{4}$$

$$P_{inj} = P_{ISI} - P_p \tag{5}$$

In the formulas, $\sigma'_z$ is the vertical effective stress, in MPa; $\sigma'_H$ is the maximum horizontal effective principal stress, in MPa; $\sigma'_h$ the minimum horizontal effective principal stress, in MPa; $\sigma_z$ is the vertical stress, in MPa; $\sigma_H$ is the maximum horizontal principal stress, in MPa; $\sigma_h$ the minimum horizontal principal stress, in MPa; $\alpha$ is the effective stress coefficient, in decimal; $\sigma_c$ is the experimental confining pressure, in MPa; $P_{inj}$ is the fluid injection pressure, in MPa; $P_{ISI}$ is the bottom-hole instantaneous shut-in pressure for the hydraulic fracturing, in MPa; $P_P$ is the formation pore pressure, in MPa.

(4) The fracturing fluid is prepared according to the fracturing fluid formula on the construction site, and poured into the intermediate container of the constant-speed and constant-pressure pump.

(5) The core after the porosity test in Step (2) is put into the core holder, and loaded with an initial confining pressure of 5 MPa by the confining pressure pump.

(6) The reaction kettle, the core and the core holder are heated by the heater to the experimental temperature determined in Step (3).

(7) The air in the pipe and the reaction kettle is completely pumped out by the vacuum pump, then the inlet valve of the vacuum pump is closed, and the fracturing fluid in the intermediate container in Step (4) is pumped by the constant-speed and constant-pressure pump into the reaction kettle.

(8) The linear velocity of the fracturing fluid on the fracture surface is calculated with the formula (6) according to the fracturing displacement of the shale gas well, the shale reservoir thickness, and the hydraulic fracture width. The experimental loading velocity is calculated with the formula (7) according to the relationship between the linear velocity and the rotation speed. The motor is switched on to load the rotor to the set rotation speed.

$$v = \frac{Q}{hw} \tag{6}$$

$$n = \frac{v}{2\pi r} \tag{7}$$

In the formulas, v is the linear velocity of fluid, in m/s, Q is the fracturing displacement of the shale gas well, in m³/min, h is the thickness of the reservoir where the shale gas well is located, in m, w is the hydraulic fracture width, in m, n is the loading speed, in rad/min, and r is the rotor radius, in m.

(9) The injection pressure of the constant-speed and constant-pressure pump is set according to the loading pressure of the confining pressure pump that is determined in Step (3) and the determined injection pressure. At the same time, the control computer of the constant-speed and constant-pressure pump records the injected fluid volume once every three minutes. The cumulative volume of each time node is the dynamic imbibition amount of the shale at that time. The test time is the average single-stage fracturing time of the shale gas well.

(10) According to the dynamic imbibition amount measured in Step (9), the dynamic imbibition saturation is defined to characterize the dynamic imbibition amount, that is, the percentage I of the dynamic imbibition amount to the core pore volume, expressed as follows:

$$I = \frac{V}{\varphi AL} \times 100\% \tag{8}$$

In the formula: I is the dynamic imbibition saturation, that is, the dynamic imbibition capacity, in %, V is the dynamic imbibition amount, in cm$^3$, A is the imbibition area, in cm$^2$, L is the core length, in cm, and $\varphi$ is the porosity, in %.

Compared with the prior art, the present invention has the following beneficial effects:

(1) The present invention designs an innovative experimental device and a test method for the shale dynamic imbibition capacity considering various factors such as the fracturing fluid flow, the formation confining pressure, the formation temperature and the fluid pressure.

(2) The present invention can truly reflect and quantitatively test the change rule of the dynamic imbibition with time under different construction parameters in the shale fracturing process under different formation conditions, and define the dynamic imbibition saturation to quantitatively characterize the shale dynamic imbibition capacity, which has an important guiding role in understanding the imbibition rule of the fracturing fluid in shale reservoirs under the actual formation conditions.

In order to facilitate the understanding and application of the present invention by those skilled in the art, specific embodiments of the present invention will be described below in details with reference to the appended figures and a shale well in the southern region of the Sichuan Basin. The details are described as follows:

(1) Core preparation: The core is taken from the downhole core at the middle of 2,500~2,560 m reservoir interval of Well XX, made into a standard core (11) with a diameter of 2.5 cm and a length of 5 cm, and placed in dryer at 100° C. to dry to a constant weight. Calculated as per the end size of the core, the imbibition area A of the core is 4.9 cm2, and the core length is 5 m, equivalent to the experimental measurement length L.

(2) Physical parameter test of the shale: The porosity $\varphi$ of the dried core (11) mentioned in Step (1) is 5.12% as tested by a porosity tester with helium as the working medium.

(3) The shale formation temperature of Well XX is 82.5° C., the pore pressure of the formation is 49 MPa, the maximum principal stress of the horizontal well is 50 MPa, the minimum principal stress of the horizontal well is 42 MPa, the vertical stress is 46 MPa, the bottom-hole instantaneous shut-in pressure for the hydraulic fracturing is 52 MPa, and the effective stress coefficient is 0.5. Based on the formation temperature, the experimental temperature is determined to be 82.5° C. Calculated with the formulas (1) to (3), the experimental maximum effective principal stress of the horizontal well is determined to be 25.5 MPa, the minimum effective principal stress of the horizontal well is to be 17.5 MPa, and the vertical effective stress is to be 21.5 MPa. Calculated with the formula (4), the experimental confining pressure is determined to be 21.5 MPa. Calculated with the formula (5), the experimental injection fluid pressure is determined to be 3 MPa.

(4) The fracturing fluid is prepared at the construction site, and poured into the intermediate container 3 of the constant-speed and constant-pressure pump.

(5) The core (11) after the porosity test in Step (3) is put into the core holder (12), and loaded with an initial confining pressure of 5 MPa by the confining pressure pump (15).

(6) The reaction kettle, the core (11) and the core holder (12) are heated by the heater (10) to the experimental temperature determined in Step (3).

(7) The air in the pipe and the reaction kettle (9) is completely pumped out by the vacuum pump (5), then the inlet valve (6) of the vacuum pump is closed, and the fracturing fluid in the intermediate container (3) is pumped by the constant-speed and constant-pressure pump (1) into the reaction kettle (9).

(8) The fracturing displacement Q of Well XX is 12 m$^3$/min, the shale reservoir thickness h is 30 m, the hydraulic fracture width w is assumed to be 0.008 m, and the radius r of the experimental testing device rotor 8 is 0.036 m. Calculated with the formulas (6) and (8), the rotor speed is 221 rad/min. The motor of the experimental testing device is switched on and the rotor is loaded to 221 rad/min.

(9) The injection pressure of the constant-speed and constant-pressure pump (1) is set according the loading pressure of the confining pressure pump (15) that is determined in Step (3) and the determined injection pressure. At the same time, the control computer of the constant-speed and constant-pressure pump records the injected fluid volume once every three minutes. The cumulative volume of each time node is the dynamic imbibition amount of the shale at that time. The average single-stage fracturing time of Well XX is 5 hours, and the dynamic imbibition amount V is 0.42 cm$^3$ after 5 hours of experimental test.

Figure 2:
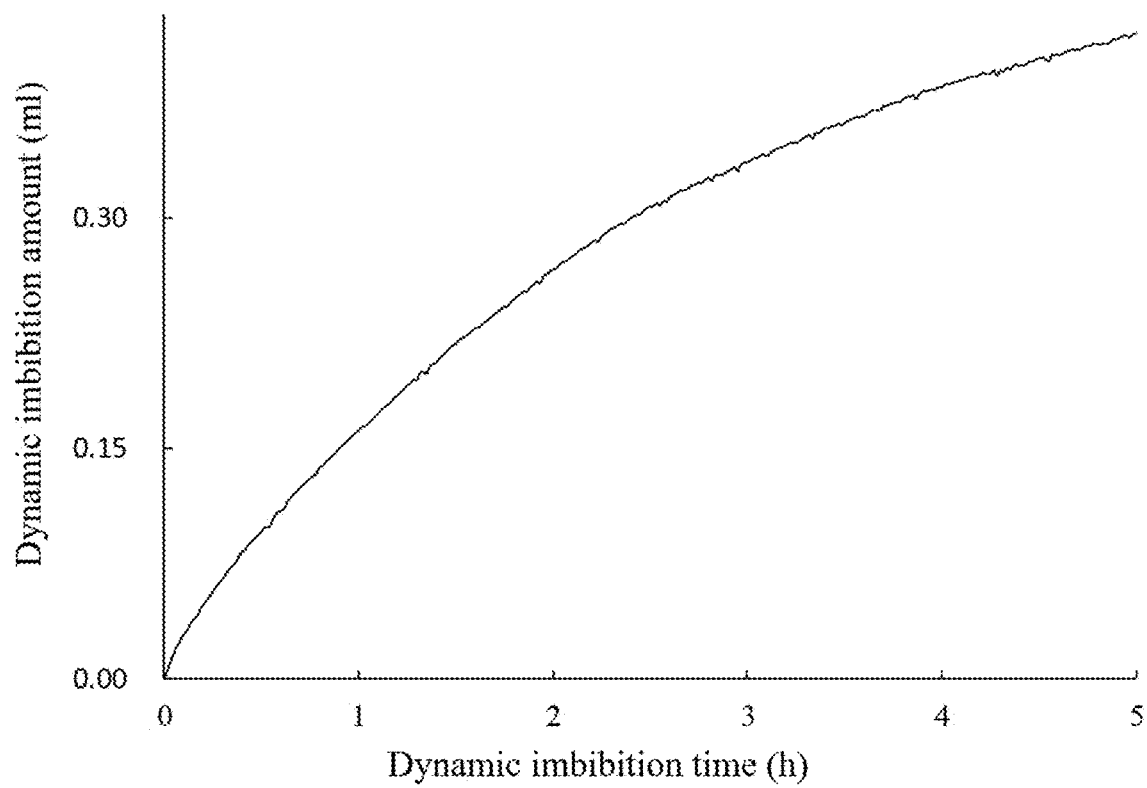
FIG. 2 is a curve of the relationship between the dynamic imbibition amount of the shale core and the time.

(10) The dynamic imbibition saturation (i.e., dynamic imbibition capacity) of the core after 5 hours of experimental test is calculated to be 33.48% with the formula (8) according to the imbibition area and length of the shale core in Step (1), the shale porosity tested in Step (2), and the curve (FIG. 2) of changes in dynamic imbibition amount with time which is tested in Step (9).

While the preferred embodiments of the present invention have been described in details with reference to the accompanying figures, they should not be construed as limiting the scope of protection of the patent. Within the scope described in the claims, various modifications and variations that can be made by those skilled in the art without creative efforts still fall within the protection scope of the patent.

What is claimed is:
1. An experimental test method for dynamic imbibition capacity of a shale, comprising:
(1) a core preparation: a core is made of a downhole rock column in a shale reservoir section of the shale or an outcrop in a same formation of the shale; an imbibition area A of the core is calculated according to an end size of the core, a core length of the core is an experimental measurement length L, and the core is dried in a dryer to a constant weight;

(2) a physical parameter test of the shale: a porosity φ of the dried core mentioned in Step (1) is tested by a porosity tester with helium as a working medium;

(3) experimental loading conditions are determined according to a formation stress, a formation temperature and a plurality of hydraulic fracturing parameters, which determines an experimental confining pressure loaded in an experiment with formulas (1) to (4), the formation temperature is an experimental temperature, and a fluid injection pressure is determined by a formula (5);

$$\sigma'_z = \sigma_z - \alpha P_p \quad (1)$$

$$\sigma'_H = \sigma_H - \alpha P_p \quad (2)$$

$$\sigma'_h = \sigma_h - \alpha P_p \quad (3)$$

$$\sigma_C = (\sigma'_z + \sigma'_H + \sigma'_h)/3 \quad (4)$$

$$P_{inj} = P_{ISI} - P_p \quad (5)$$

in the above formulas, $\sigma'_z$ is a vertical effective stress, in MPA; $\sigma'_H$ is a maximum horizontal effective principal stress, in MPa; $\sigma'_h$ is a minimum horizontal effective principal stress, in MPa; $\sigma_z$ is a vertical stress, in MPa; $\sigma_H$ is a maximum horizontal principal stress, in MPa; $\sigma_h$ is a minimum horizontal principal stress, in MPa; α is an effective stress coefficient, in decimal; $\sigma_c$ is the experimental confining pressure, in MPa; $P_{inj}$ is the fluid injection pressure, in MPa; $P_{ISI}$ is a bottom-hole instantaneous shut-in pressure for the hydraulic fracturing, in MPa; $P_P$ is a formation pore pressure, in MPa;

(4) a fracturing fluid is prepared according to a fracturing fluid formula on a construction site, and poured into an intermediate container of a constant-speed and constant-pressure pump;

(5) the core after the physical parameter test in Step (2) is put into a core holder, and loaded with an initial confining pressure by a confining pressure pump;

(6) a reaction kettle, the core and the core holder are heated by a heater to the experimental temperature determined in Step (3);

(7) an air in a pipe and the reaction kettle is completely pumped out by a vacuum pump, then an inlet valve of the vacuum pump is closed, and the fracturing fluid in the intermediate container in Step (4) is pumped by the constant-speed and constant-pressure pump into the reaction kettle;

(8) an linear velocity of the fracturing fluid on a fracture surface is calculated with a formula (6) according to a fracturing displacement of a shale gas well, a shale reservoir thickness, and a hydraulic fracture width; a loading velocity is calculated with a formula (7) according to a relationship between the linear velocity and a rotation speed; a motor is switched on to load a rotor to the rotation speed;

$$v = \frac{Q}{hw}; \quad (6)$$

$$n = \frac{v}{2\pi r}; \quad (7)$$

in the above formulas, v is the linear velocity of the fracturing fluid, in m/s; Q is the fracturing displacement of the shale gas well, in m³/min; h is the shale reservoir thickness where the shale gas well is located, in m; w is the hydraulic fracture width, in m; n is the loading velocity, in rad/min; and r is a rotor radius, in m;

(9) the fluid injection pressure of the constant-speed and constant-pressure pump is set according to the experimental confining pressure of the confining pressure pump that is determined in Step (3) and the determined injection pressure; a control computer of the constant-speed and constant-pressure pump records an injected fluid volume once every three minutes; a cumulative volume of each time node is a dynamic imbibition amount of the shale; a test time is an average single-stage fracturing time of the shale gas well; and

(10) according to the dynamic imbibition amount measured in Step (9), a dynamic imbibition saturation I is defined to characterize the dynamic imbibition amount, which is expressed as follows:

$$I = \frac{V}{\varphi AL} \times 100\%; \quad (8)$$

in the above formula: I is the dynamic imbibition saturation, in %; V is the dynamic imbibition amount, in cm³; A is the imbibition area, in cm²; L is the core length, in cm; and φ is the porosity, in %.

* * * * *